US011959909B2

(12) United States Patent
Choi et al.

(10) Patent No.: US 11,959,909 B2
(45) Date of Patent: Apr. 16, 2024

(54) BASAL GANGLIA-ON-CHIP FOR SCREENING THERAPEUTIC AGENTS FOR BRAIN AND NERVOUS SYSTEM DISEASES

(71) Applicant: Sogang University Research Foundation, Seoul (KR)

(72) Inventors: Jeong-Woo Choi, Seoul (KR); Won Jun Lee, Gyeonggi-do (KR); Jae Wook Shin, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 1105 days.

(21) Appl. No.: 16/426,795

(22) Filed: May 30, 2019

(65) Prior Publication Data

US 2019/0369089 A1 Dec. 5, 2019

(30) Foreign Application Priority Data

May 31, 2018 (KR) ........................ 10-2018-0063027

(51) Int. Cl.

*G01N 33/50* (2006.01)
*A61P 25/00* (2006.01)
*B01J 19/00* (2006.01)
*B01L 3/00* (2006.01)
*B33Y 10/00* (2015.01)
*B33Y 70/10* (2020.01)
*B33Y 80/00* (2015.01)
*C12M 1/12* (2006.01)
*C12M 3/00* (2006.01)

(52) U.S. Cl.

CPC .......... *G01N 33/5058* (2013.01); *A61P 25/00* (2018.01); *B01J 19/0093* (2013.01); *B01L 3/5027* (2013.01); *B33Y 10/00* (2014.12); *B33Y 70/10* (2020.01); *B33Y 80/00* (2014.12); *C12M 21/08* (2013.01); *C12M 25/14* (2013.01)

(58) Field of Classification Search

CPC ......... G01N 33/54386; G01N 33/5308; G01N 33/6896; G01N 2400/02; G01N 2400/10; A61B 5/4064; A61B 10/0051; A61B 10/007

See application file for complete search history.

(56) References Cited

FOREIGN PATENT DOCUMENTS

KR 10-2009-0110101 A 10/2009
KR 10-2016-0150173 A 12/2016

OTHER PUBLICATIONS

Dequach et al. Tissue Engineering: Part A, vol. 17, Nos. 21 and 22, 2011 (Year: 2011).*
Huang et al., Scientific Reports, 7:40772, 2016 (Year: 2016).*
Min et al., Materials, 10, 1151, published Oct. 2, 2017 (Year: 2017).*
Zhou et al. Carbon, 116:615-624, 2017 (Year: 2017).*
Zhang et al., PNAS, vol. 113, No. 12: 3185-3190, (2016) (Year: 2016).*
Polak et al., Nanomedicine: Nanotech. Biol. & Med., 11:1467-79, (2015) (Year: 2015).*
Potjewyd, G., et al., "Tissue Engineering 3D Neurovascular Units: A Biomaterials and Bioprinting Perspective." *Trends Biotechnol.*, 2018; 36(4):457-72.
Wang, X., et al., "Gelatin-Based Hydrogels for Organ 3D Bioprinting.", *Polymers*, 2017; 9:401.
Notice of Allowance from corresponding Korean Patent Application No. 10-2018-0063027, issued on Dec. 16, 2019.
Zhang, Y., et al.; "Influence of pulsed electromagnetic field with different pulse duty cycles on neurite outgrowth in PC12 rat pheochromocytoma cells", Bioelectromagnetics. Jul. 2005;26(5):406-11. (Abstract Only).

* cited by examiner

*Primary Examiner* — Kimberly Ballard
*Assistant Examiner* — Stacey N MacFarlane
(74) *Attorney, Agent, or Firm* — Harness, Dickey & Pierce, P.L.C.

(57) ABSTRACT

The present disclosure provides a basal ganglia-on-a-chip for screening therapeutic agents for brain and nervous system diseases and a method for fabricating the same. The present invention provides a method for screening therapeutic agents for dopamine-dependent brain and nervous system diseases by using a basal ganglia-on-a-chip. When the basal ganglia-on-a-chip of the present invention is used in the effect evaluation of therapeutic agents for brain and nervous system diseases, the effect evaluation of therapeutic candidate substances can be economically and promptly carried out compared with an existing technique.

9 Claims, 19 Drawing Sheets

BASAL GANGLIA-ON-CHIP FOR SCREENING THERAPEUTIC AGENTS FOR BRAIN AND NERVOUS SYSTEM DISEASES

CROSS-REFERENCE TO RELATED APPLICATION

This application claims priority to and the benefit of Korean Patent Application No. 10-2018-0063027 filed in the Korean Intellectual Property Office on 31 May 2018, the disclosure of which is incorporated herein by reference.

FIELD

The present disclosure relates to a basal ganglia-on-a-chip for screening therapeutic agents for brain and nervous system diseases.

BACKGROUND

The organ-on-a-chip technology that mimicking the organ by placing an organ-specific cells on a chip is attracting people's interest as a widely applicable technology in medical fields, such as studies on pathogenesis of human diseases and drug screening associated with disease therapeutic agents. Various organs-on-chips has been designed for lung, bowels, and liver and studied to reduce the cost and time for the drug screening, which is an essential step in a drug development procedures. However, in case of a brain-on-a-chip, it was extremely challenging to develop it because of the complicatedly connected neural network structures. To this end, a brain-on-a-chip based research for neurodegenerative diseases, such as Parkinson's disease and Alzheimer's disease, has been studied limitedly.

In order to overcome such limitations, various techniques have been utilized, such as, micro-fluidic chips and cell patterning. These techniques have been used to mimic horizontal connections of neural networks. The horizontal growth of cells was guided by microchannel of a microfluidic chip or patterned growth factors on the substrate. There are limits to mimic the vertical connections of neural networks. Therefore, for the study of a brain-on-a-chip reflecting horizontal and vertical connections of neural networks, the connection with other technologies are necessary.

3D printers have been applied to various fields due to a wide range of usability, and recently, technologies for forming a structure by cell printing have been studied. The utilization of 3D cell printers can produce a more sophisticated structure compared with existing pipettes-based three-dimensional cell culture technology. Cell-friendly three-dimensional cell structures can be formed by utilizing gelatin-methacrylate harmless to cells. Therefore, such a technique can be utilized as a technique suitable for fabricating a brain-on-a-chip by mimicking a complex neural network structure.

Various attempts have been made to control the vertical growth of neural networks, which is a key element in the fabrication of a brain-on-a-chip model. Out of these, a technique of utilizing magnetic nanoparticles has receiving an attraction. The technique is that magnetic nanoparticles are attached to an antibody capable of attaching to a surface of cells, and then the antibody is attached to cells. The vertical application of a magnetic field can vertically induce the growth direction of cells along the direction of the magnetic field. Such a technique is evaluated as a key technique capable of simulating the vertical connection of neural networks in the brain.

The fusion of such techniques will replace existing Parkinson's disease models causing an ethical issue and requiring lots of costs and times, such as a neurotoxic model induced by the administration of environmental toxins or synthetic toxins and a genetic animal model fabricated through the modification of genes, such as α-synuclein, Parkin, Pink1, DJ-1, and LRRK2.

PRIOR ART DOCUMENTS

Patent Documents (Patent Document 1) Korean Patent Publication No. 2016-0150173

(Patent Document 2) Korean Patent Publication No. 2009-0110101

Non-Patent Documents (Non-Patent Document 1) Potjewyd Get al. Trends Biotechnol. 2018; 36(4): 457-72

(Non-Patent Document 1) X Wang et al. Polymers 2017; 9:401

SUMMARY

Technical Problem

The present inventors have made research efforts to develop a basal ganglia-on-a-chip for screening therapeutic agents for brain and nervous system diseases, such as Parkinson's disease caused due to dopamine deficiency. As a result, the present inventors manufactured a basal ganglia-on-a-chip having neural networks simulating a direct neural circuit and an indirect neural circuit in the basal ganglia and confirmed a use thereof for screening therapeutic agents for brain and nervous system diseases, and then completed the present invention.

Therefore, an aspect of the present invention is to provide a basal ganglia-on-a-chip for screening therapeutic agents for brain and nervous system diseases.

Another aspect of the present invention is to provide a method for screening therapeutic agents for brain and nervous system diseases by using a basal ganglia-on-a-chip.

Still another aspect of the present invention is to provide a method for fabricating a basal ganglia-on-a-chip for screening a therapeutic drug for brain and nervous system diseases.

Technical Solution

In accordance with an aspect of the present invention, there is provided a basal ganglia-on-a-chip for screening therapeutic agents for brain and nervous system diseases, the basal ganglia-on-a-chip including:

(a) graphene-conjugated magnetic nanoparticles patterned on a substrate;

(b) (i) a first hydrogel containing glutamatergic neurons and (ii) a second hydrogel containing GABAergic neurons, the first and second hydrogels being disposed in parallel on a pattern of the graphene-conjugated magnetic nanoparticles;

(c) a third hydrogel in contact with the second hydrogel, the third hydrogel containing GABAergic neurons and neuronal membrane protein-specific antibody-conjugated magnetic nanoparticles; and (d) a fourth hydrogel in contact with the third hydrogel, the fourth hydrogel containing dopaminergic neurons and neuronal membrane protein-specific antibody-conjugated magnetic nanoparticles.

The present inventors have made research efforts to develop a basal ganglia-on-a-chip for screening therapeutic agents for brain and nervous system diseases, such as Parkinson's disease caused due to dopamine deficiency. As a result, the present inventors manufactured a basal ganglia-on-a-chip having neural networks simulating a direct neural circuit and an indirect neural circuit in the basal ganglia and confirmed a use thereof for screening therapeutic agents for brain and nervous system diseases, and then completed the present invention.

As used herein, the term "brain and nervous system diseases" refers to diseases that are caused by the damage to brain neurons by physiological, physical, and mechanical factors.

In an embodiment of the present invention, the brain and nervous system diseases are dopamine-dependent brain and nervous system diseases.

As used herein, the term "dopamine-dependent brain and nervous system diseases" refers to diseases that are caused by dopamine deficiency or excess or cause aggravation of symptoms thereby in the central nervous system.

In an embodiment of the present invention, the brain and nervous system diseases caused by dopamine deficiency are brain and nervous system diseases selected from the group consisting of Parkinson's disease, neurocognitive function disorders, attention-deficit/hyperactivity disorder, depression, and restless leg syndrome.

As used herein, the term "Parkinson's disease" is a representative brain nervous system disease that is caused by a decrease in dopamine levels and characterized by stable tremor, stiffness, slowness of movement (slow movement), and postural instability. In addition, Parkinson's disease has clinical symptoms, such as autonomic nervous system symptoms, neuropsychiatric symptoms, cognitive dysfunctions, sleep disorders, pain, fatigue, olfactory disorder, gastrointestinal disorders, salivation, difficulty in swallowing, constipation, orthostatic hypotension, hyperhidrosis, dysuria, and dry eye.

As used herein, the term "neurocognitive function disorders" refers to a condition in which memory, attention, language ability, time-space capability, judgment, and the like are degraded. In the frontal lobe, dopamine controls the flow of information from other regions of the brain. The dopamine disorder in this region of the brain may affect neurocognitive functions, especially, memory, attention, and problem-solving functions. The dopamine deficiency in the prefrontal cortex may cause neurocognitive function disorders.

As used herein, the term "attention-deficit/hyperactivity disorder (ADHD)" refers to a mental syndrome having distracted attention, excessive activity, impulsivity, and learning disability. The existing ADHD medicine methylphenidate activates dopamine and norepinephrine, which are brain neurotransmitters in charge of attention concentration, to enhance attention and concentration.

As used herein, the term "depression" refers to a disease that causes "negative emotions" due to a change in brain functions controlling emotions. The depression is caused by a chemical imbalance of neurotransmitters, such as dopamine, serotonin, and norepinephrine.

As used herein, the term "restless leg syndrome" refers to a disease that has symptoms of an uncomfortable sensation and impatience in the legs and an urge to move the legs during a rest, usually when lying or sitting, wherein such symptoms get worse, causing sleep disorders, especially, at night. Restless legs syndrome is presumed to be caused by a deficiency of dopamine, and the symptoms are alleviated by treatment with a dopamine preparation.

As used herein, the term "brain and nervous system diseases caused by dopamine excess" refers to diseases that are caused by dopamine excess or an increase in dopamine levels or cause aggravation of symptoms thereby in the central nervous system. A major cause of dopamine excess and an increase in dopamine levels is a reduction in dopamine receptors and the overproduction of dopaminergic neurons or dopamine.

In an embodiment of the present invention, the brain and nervous system diseases caused by dopamine excess are brain and nervous system diseases selected from the group consisting of manic-depression, schizophrenia, and anxiety disorder.

As used herein, the term "manic-depression (bipolar disorder)" refers to a disease causing the periodic alternation of a manic episode corresponding to an abnormal excitement condition and a depressive episode corresponding to an abnormal depression condition, meaning an endogenous mental disease having a mode disorder as a main symptom. The manic-depression is known to be caused by changes in levels of dopamine present in the brain and the dysfunction caused thereby.

As used herein, the term "schizophrenia" refers to a brain disease causing a mentally disturbed state. In the brain, a number of neurotransmitters that control thinking, emotions, and behaviors are secreted to transmit information between cells. Patients with schizophrenia have symptoms since the neurotransmission process of the substance dopamine is problematic in a site of the brain, in which the activation of dopamine results in delusions, auditory hallucination, and confused thinking.

As used herein, the term "anxiety disorder" refers to a disease that causes excessive psychological distress or severe difficulty in realistic adaptation due to pathological anxiety, wherein the disease includes generalized anxiety disorder, social phobia, panic disorder, and post-traumatic stress disorder.

The basal ganglia-on-a-chip for screening therapeutic agents for brain and nervous system diseases of the present invention will be described by elements.

(a) Graphene-Conjugated Magnetic Nanoparticles

The basal ganglia-on-a-chip for screening therapeutic agents for brain and nervous system diseases of the present invention includes graphene-conjugated magnetic nanoparticles (magnetic/graphene hybrid nanostructures) patterned on a substrate.

The graphene-conjugated magnetic nanoparticles form a self-assembled monolayer on the substrate through microcontact printing.

In an embodiment of the present invention, the substrate is formed of a metal, a silicone, a metal oxide, glass, a ceramic, quartz, a semiconductor, a $Si/SiO_2$ wafer, germanium, gallium arsenide, carbon, carbon nanotubes, a polymer, Sepharose, or agarose.

In another embodiment of the present invention, the substrate is formed of a silicone.

In a particular embodiment of the present invention, the substrate is formed of polydimethylsiloxane (PDMS).

The graphene-conjugated magnetic nanoparticle may be prepared by the combination of a modified amine group on the surface of the magnetic nanoparticle and a carboxyl group of a graphene oxide.

The graphene-conjugated magnetic nanoparticles function to induce the horizontal growth of neurons.

When the graphene-conjugated magnetic nanoparticles are patterned on the substrate, a magnetic field is applied in a vertical direction to allow glutamatergic neurons and GABAergic neurons to grow in a horizontal direction.

According to an embodiment of the present invention, the application of the magnetic field may be performed with a magnetic field of 100-1000 mT, 200-1000 mT, 300-1000 mT, 400-1000 mT, 100-900 mT, 100-800 mT, 100-700 mT, 100-600 mT, 100-500 mT, 200-900 mT, 200-800 mT, 300-700 mT, 300-600 mT, 400-500 mT, or 400-450 mT.

(b) First Hydrogel Containing Glutamatergic Neurons and Second Hydrogel Containing GABAergic Neurons The basal ganglia-on-a-chip for screening therapeutic agents for brain and nervous system diseases of the present invention includes a first hydrogel containing glutamatergic neurons and a second hydrogel containing GABAergic neurons, on graphene-conjugated magnetic nanoparticles patterned on the substrate.

The second hydrogel is disposed adjacent to one side surface of the first hydrogel.

The glutamatergic neurons contained in the first hydrogel correspond to neurons of the "subthalamic nucleus" in the basal ganglia.

The GABAergic neurons contained in the second hydrogel correspond to neurons of the "globus pallidus interna" in the basal ganglia.

The second hydrogel containing GABAergic neurons may be printed on the pattern of graphene-conjugated magnetic nanoparticles such that the second hydrogel is adjacent to one side surface of the first hydrogel containing glutamatergic neurons.

The printing may be performed using a 3D printer.

The first hydrogel and the second hydrogel are composed of a polymer suitable for the growth of neurons.

In an embodiment of the present invention, the first hydrogel and the second hydrogel contain at least one hydrogel monomer selected from the group consisting of gelatin methacrylate (GelMA), acrylic acid, acrylamide acrylate, N-isopropylacrylamide (NIPAAM), and polyethylene glycol diacrylate (PEGDA).

In another embodiment of the present invention, the first hydrogel and the second hydrogel contain a hydrogel monomer of gelatin methacrylate.

The first hydrogel and the second hydrogel have structural stability suitable for the growth of neurons.

According to one embodiment of the present invention, the first hydrogel and the second hydrogel have a concentration of gelatin methacrylate of more than 3.9% and less than 5.0%.

According to another embodiment of the present invention, the first hydrogel and the second hydrogel have a concentration of gelatin methacrylate of more than 3.0% and less than 4.8%, more than 3.0% and less than 4.6%, more than 3.0% and less than 4.4%, more than 3.0% and less than 4.2%, more than 3.2% and less than 5.0%, more than 3.4% and less than 5.0%, more than 3.6% and less than 5.0%, more than 3.8% and less than 5.0%, more than 3.2% and less than 4.8%, more than 3.4% and less than 4.6%, more than 3.6% and less than 4.4%, or more than 3.8% and less than 4.2%.

A concentration of gelatin methacrylate of 3.0 or less results in structural instability, and thus is not suitable for the growth of neurons. A concentration of gelatin methacrylate of 5.0 or more results in a reduction in the growth of neurons.

The first hydrogel and the second hydrogel contain brain-derived extracellular matrix for promoting the growth of neuronal axons.

According to an embodiment of the present invention, the first hydrogel and the second hydrogel contain mammalian brain-derived extracellular matrix. The mammal may be at least one mammal selected from the group consisting of pig, horse, cow, dog, rabbit, cat, sheep, mountain goat, goat, deer, bear, tiger, lion, monkey, gorilla, chimpanzee, wolf, fox, and rat.

According to another embodiment of the present invention, the first hydrogel and the second hydrogel further contain brain-derived extracellular matrix.

According to an embodiment of the present invention, the first hydrogel and the second hydrogel may further contain decellularized brain matrix (DECM).

According to an embodiment of the present invention, the DECM is decellularized mammalian brain extracellular matrix.

In a particular embodiment of the present invention, the DECM is decellularized porcine brain extracellular matrix.

As used herein, the term "extracellular matrix" is the matrix that surrounds the outsides of cells, occupies between a cell and a cell, and has a network structure mainly composed of proteins and polysaccharides. The components of the extracellular matrix are classified into: structural component, such as collagen and elastin; adhesive proteins, such as fibronectin, bitronectin, laminin, and tenacin; chondroitin sulfate, heparan sulfate, and proteoglycans produced from main proteins; and hyaluronic acid composed of only polysaccharides. These extracellular matrix components not only determine the type of tissue composed of cell aggregation, but also provide an environment in which cells can function normally, and are also main substances involved in cell differentiation.

The treatment of a culture medium for culturing neurons or a hydrogel with the DECM lowers the growth rate of neurons and further elongates neuronal axons.

According to an embodiment of the present invention, the DECM may be contained in 0.001-0.1%, 0.003-0.1%, 0.001-0.08%, 0.001-0.06%, 0.001-0.04%, 0.001-0.02%, 0.003-0.08%, 0.003-0.06%, 0.003-0.04%, 0.003-0.02%, or 0.005-0.02% in the culture medium for culturing neurons or the hydrogel.

(c) Third Hydrogel Containing GABAergic Neurons and Neuronal Membrane Protein-Specific Antibody-Conjugated Magnetic Nanoparticles The basal ganglia-on-a-chip for screening therapeutic agents for brain and nervous system diseases of the present invention includes a third hydrogel in contact with the second hydrogel, the third hydrogel containing GABAergic neurons and neuronal membrane protein-specific antibody-conjugated magnetic nanoparticles.

The GABAergic neurons contained in the third hydrogel correspond to neurons of "striatum" in the basal ganglia.

The neuronal membrane protein-specific antibody-conjugated magnetic nanoparticles function to induce the vertical growth of neurons.

The neuronal membrane protein-specific antibody-conjugated magnetic nanoparticles bind to cell membrane proteins of neurons to induce the growth of neurons in a direction in which a magnetic field is applied.

In an embodiment of the present invention, the antibody specific to cell membrane proteins bound to the neuronal membrane protein-specific antibody-conjugated magnetic nanoparticles is an antibody specific to membrane receptors, transport proteins, membrane enzymes, or cell adhesion molecules in neurons.

In another embodiment of the present invention, the antibody specific to cell membrane proteins bound to the neuronal membrane protein-specific antibody-conjugated magnetic nanoparticles is an antibody specific to a transport protein.

In a particular embodiment of the present invention, the antibody specific to cell membrane proteins bound to the neuronal membrane protein-specific antibody-conjugated magnetic nanoparticles is an antibody specific to a noradrenaline transport.

Since the third hydrogel has the same composition as the first hydrogel and the second hydrogel in view of the other composition excluding GABAergic neurons and neuronal membrane protein-specific antibody-conjugated magnetic nanoparticles, the overlapping description therebetween will be omitted to avoid excessive complexity of the specification.

(d) Fourth Hydrogel Containing Dopaminergic Neurons and Neuronal Membrane Protein-Specific Antibody-Conjugated Magnetic Nanoparticles The basal ganglia-on-a-chip for screening therapeutic agents for brain and nervous system diseases of the present invention includes a fourth hydrogel in contact with the third hydrogel, the fourth hydrogel containing dopaminergic neurons and neuronal membrane protein-specific antibody-conjugated magnetic nanoparticles.

The dopaminergic neurons contained in the fourth hydrogel correspond to neurons of "substantia nigra pars compacta" in the basal ganglia.

Since the fourth hydrogel has the same composition as the third hydrogel in view of the other composition excluding dopaminergic neurons, the overlapping description therebetween will be omitted to avoid excessive complexity of the specification.

In accordance with another aspect of the present invention, there is provided a method for screening therapeutic agents for brain and nervous system diseases by using a basal ganglia-on-a-chip, the method comprising:

(a) treating dopaminergic neurons with a candidate of therapeutic agents for brain and nervous system diseases; and (b) investigating whether the dopaminergic neurons proliferate or are reduced.

The method for screening therapeutic agents for brain and nervous system diseases by using a basal ganglia-on-a-chip in the present invention will be described by steps.

(a) Treating Dopaminergic Neurons with a Candidate of Therapeutic Agents for Brain and Nervous System Diseases Dopaminergic neurons are treated with a candidate of therapeutic agents for brain and nervous system.

In an embodiment of the present invention, the dopaminergic neurons are induced to have damages.

The damages will be caused by oxidative stress. The oxidative stress will be induced by 6-hydroxydopamine (6-OHDA).

The damages are induced to dopaminergic neurons in the basal ganglia-on-a-chip, the basal ganglia-on-a-chip including: (a) graphene-conjugated magnetic nanoparticles patterned on a substrate; (b) (i) a first hydrogel containing glutamatergic neurons and (ii) a second hydrogel containing GABAergic neurons, the first and second hydrogels being disposed in parallel on a pattern of the graphene-conjugated magnetic nanoparticles; (c) a third hydrogel in contact with the second hydrogel, the third hydrogel containing GABAergic neurons and neuronal membrane protein-specific antibody-conjugated magnetic nanoparticles; and (d) a fourth hydrogel in contact with the third hydrogel, the fourth hydrogel containing dopaminergic neurons and neuronal membrane protein-specific antibody-conjugated magnetic nanoparticles.

In another embodiment of the present invention, the dopaminergic neurons are induced to differentiate.

The differentiation of the dopaminergic neurons will be induced by L-3,4-dihydroxyphenylalanine (L-dopa).

The differentiation is induced to dopaminergic neurons in the basal ganglia-on-a-chip, the basal ganglia-on-a-chip including: (a) graphene-conjugated magnetic nanoparticles patterned on a substrate; (b) (i) a first hydrogel containing glutamatergic neurons and (ii) a second hydrogel containing GABAergic neurons, the first and second hydrogels being disposed in parallel on a pattern of the graphene-conjugated magnetic nanoparticles; (c) a third hydrogel in contact with the second hydrogel, the third hydrogel containing GABAergic neurons and neuronal membrane protein-specific antibody-conjugated magnetic nanoparticles; and (d) a fourth hydrogel in contact with the third hydrogel, the fourth hydrogel containing dopaminergic neurons and neuronal membrane protein-specific antibody-conjugated magnetic nanoparticles.

(b) Investigating Whether the Dopaminergic Neurons Proliferate or Are Reduced

The effect of the candidate is evaluated by investigating whether the dopaminergic neurons in the fourth hydrogel in the basal ganglia-on-a-chip proliferate or are reduced.

When the proliferation of the dopaminergic neurons is increased compared with a control group treated without the candidate, the candidate is determined as a therapeutic drug for the brain and nervous system diseases caused by dopamine deficiency.

When the proliferation of the dopaminergic neurons is reduced compared with a control group treated without the candidate, the candidate is determined as a therapeutic drug for the brain and nervous system diseases caused by dopamine excess.

In accordance with still another aspect of the present invention, there is provided a method for fabricating a basal ganglia-on-a-chip for screening therapeutic agents for brain and nervous system diseases, the method including:

(a) patterning graphene-conjugated magnetic nanoparticles on a substrate while a magnetic field is applied to the substrate in a vertical direction;

(b) printing a first bio-ink on a pattern of the graphene-conjugated magnetic nanoparticles while a magnetic field is applied to the pattern in a vertical direction, the first bio-ink containing glutamatergic neurons and a hydrogel;

(c) printing a second bio-ink on the pattern of the graphene-conjugated magnetic nanoparticles while a magnetic field is applied to the pattern in a vertical direction, such that the second bio-ink is adjacent to one side surface of a region printed with the first bio-ink, the second bio-ink containing GABAergic neurons and a hydrogel;

(d) printing a third bio-ink on a region printed with the second bio ink in step (c), the third bio-ink containing GABAergic neurons, neuronal membrane protein-specific antibody-conjugated magnetic nanoparticles, and a hydrogel;

(d) printing a fourth bio-ink on a region printed with the third bio-ink in step (d), the fourth bio-ink containing dopaminergic neurons, neuronal membrane protein-specific antibody-conjugated magnetic nanoparticles, and a hydrogel; and (f) applying a magnetic field in a vertical direction from below the substrate.

The hydrogels in steps (b), (c), (d), and (e) are formed of a polymer suitable for the growth of neurons.

In an embodiment of the present invention, the hydrogels contain at least one hydrogel monomer selected from the group consisting of gelatin methacrylate (GelMA), acrylic acid, acrylamide acrylate, N-isopropylacrylamide (NIPAAM), and polyethylene glycol diacrylate (PEGDA).

In another embodiment of the present invention, the hydrogels contain a hydrogel monomer of gelatin methacrylate. The hydrogels have structural stability suitable for the growth of neurons.

According to an embodiment of the present invention, the hydrogels have a concentration of gelatin methacrylate of more than 3.0% and less than 5.0%.

According to another embodiment of the present invention, the first hydrogel and the second hydrogel have a concentration of gelatin methacrylate of more than 3.0% and less than 4.8%, more than 3.0% and less than 4.6%, more than 3.0% and less than 4.4%, more than 3.0% and less than 4.2%, more than 3.2% and less than 5.0%, more than 3.4% and less than 5.0%, more than 3.6% and less than 5.0%, more than 3.8% and less than 5.0%, more than 3.2% and less than 4.8%, more than 3.4% and less than 4.6%, more than 3.6% and less than 4.4%, or more than 3.8% and less than 4.2%.

A concentration of gelatin methacrylate of 3.0 or less results in structural instability, and thus is not suitable for the growth of neurons. A concentration of gelatin methacrylate of 5.0 or more results in a reduction in the growth of neurons.

The hydrogels further contain brain-derived extracellular matrix for promoting the growth of neuronal axons.

According to an embodiment of the present invention, the first hydrogel and the second hydrogel contain mammalian brain-derived extracellular matrix. The mammal may be at least one mammal selected from the group consisting of pig, horse, cow, dog, rabbit, cat, sheep, mountain goat, goat, deer, bear, tiger, lion, monkey, gorilla, chimpanzee, wolf, fox, and rat.

According to another embodiment of the present invention, the first hydrogel and the second hydrogel further contain porcine brain-derived extracellular matrix.

According to a particular embodiment of the present invention, the first hydrogel and the second hydrogel may further contain decellularized porcine brain matrix (DECM).

The DECM is decellularized mammalian brain extracellular matrix.

The DECM lowers the growth rate of neurons and further elongates neuronal axons.

The first bio-ink in step (b), the second bio-ink in step (c), the third bio-ink in step (d), and the fourth bio-ink in step (e) may be printed through three-dimensional (3D) bio-printing. The three-dimensional bio-printing refers to a technique by which a three-dimensional structure designed by a computer is fabricated by using various kinds of cells, biomaterials, and biomolecules.

As used herein, the term "bio-ink" refers to a material, which contains living cells and/or bio-molecules and allows the fabrication of a desired structure through the application of bio-printing. The bio-ink needs to provide physical properties for 3D processing and biological environments for allowing cells to perform desired functions therein.

According to an embodiment of the present invention, the first bio-ink in step (b), the second bio-ink in step (c), the third bio-ink in step (d), and the fourth bio-ink in step (e) contain more than 3.5% and less than 5.0% of gelatin methacrylate for providing physical properties for 3D processing and DECM for performing functions of neurons.

Step (f) of applying a magnetic field in a vertical direction from below the substrate allows the GABAergic neurons and dopaminergic neurons to grow in a vertical direction.

According to an embodiment of the present invention, the application of the magnetic field may be carried out with a magnetic field of 100-1000 mT, 200-1000 mT, 300-1000 mT, 400-1000 mT, 100-900 mT, 100-800 mT, 100-700 mT, 100-600 mT, 100-500 mT, 200-900 mT, 200-800 mT, 300-700 mT, 300-600 mT, 400-500 mT, or 400-450 mT.

Since the method for fabricating a basal ganglia-on-a-chip for screening therapeutic agents for brain and nervous system diseases includes the same or similar elements compared with the above-described basal ganglia-on-a-chip for screening therapeutic agents for brain and nervous system diseases, the overlapping description therebetween will be omitted to avoid excessive complexity of the specification.

Advantageous Effects

Features and advantages of the present invention are summarized as follows.

(a) The present invention provides a basal ganglia-on-a-chip for screening therapeutic agents for brain and nervous system diseases and a method for fabricating the same.

(b) The present invention provides a method for screening therapeutic agents for dopamine-dependent brain and nervous system diseases by using a basal ganglia-on-a-chip.

(c) When the basal ganglia-on-a-chip of the present invention is used in the effect evaluation of therapeutic agents for brain and nervous system diseases, the effect evaluation of therapeutic candidate substances can be economically and promptly carried out compared with an existing technique.

Figure 2A:
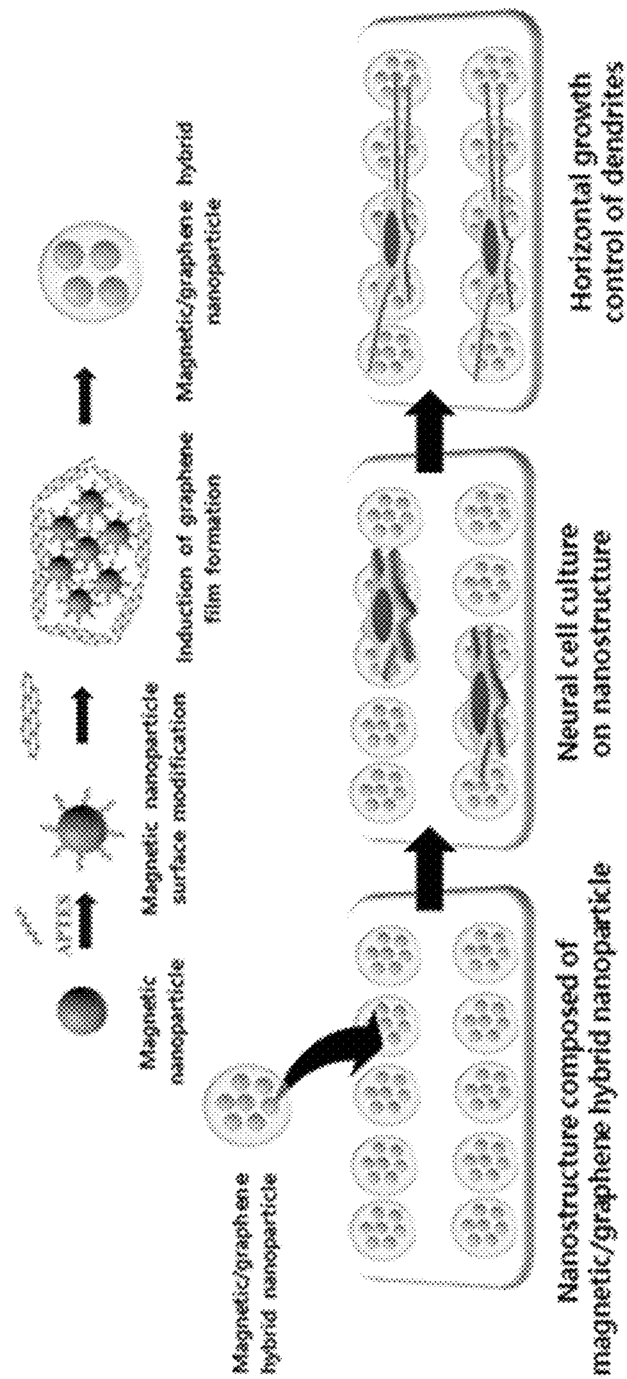
FIG. 2A schematically illustrates the vertical growth of neurons using magnetic nanoparticles with an anti-noradrenaline transporter antibody attached thereto.
Figure 2B:
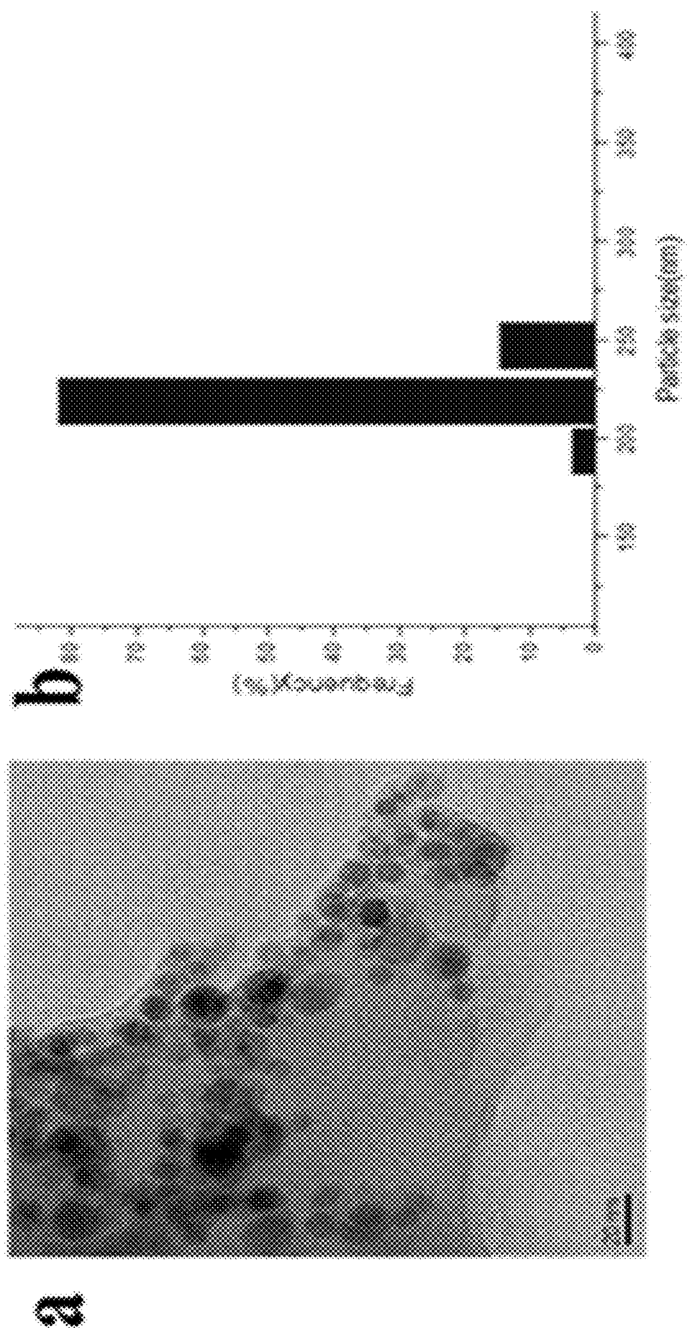
FIG. 2B illustrates the results that the treatment of cells with magnetic nanoparticles with an anti-noradrenaline transporter antibody attached thereto induced the vertical growth of the cells.
Figure 2C:
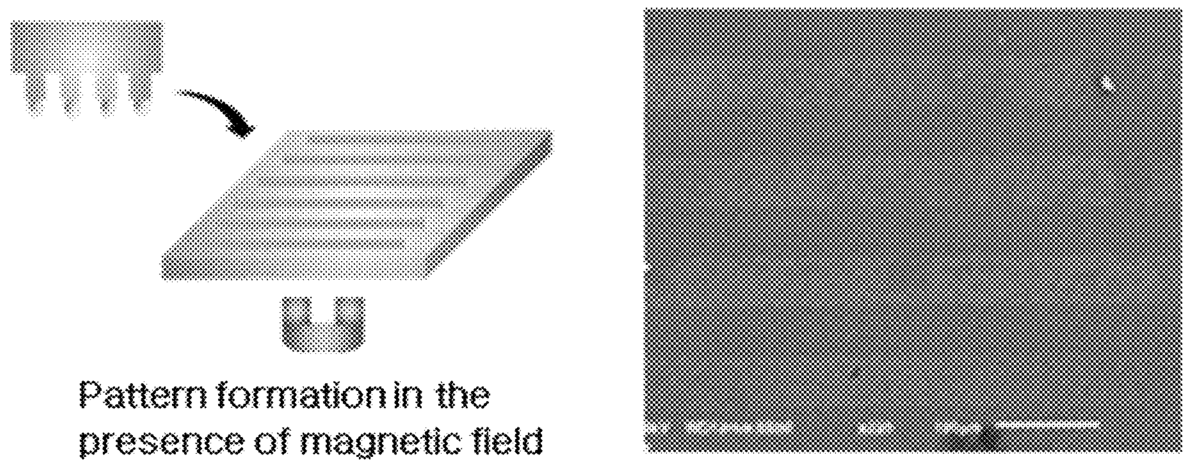
FIG. 2C illustrates the results obtained by analyzing, using a confocal microscope, the induction of vertical growth of cells through the treatment of cells with magnetic nanoparticles with an anti-noradrenaline transporter antibody attached thereto.
Figure 2D:
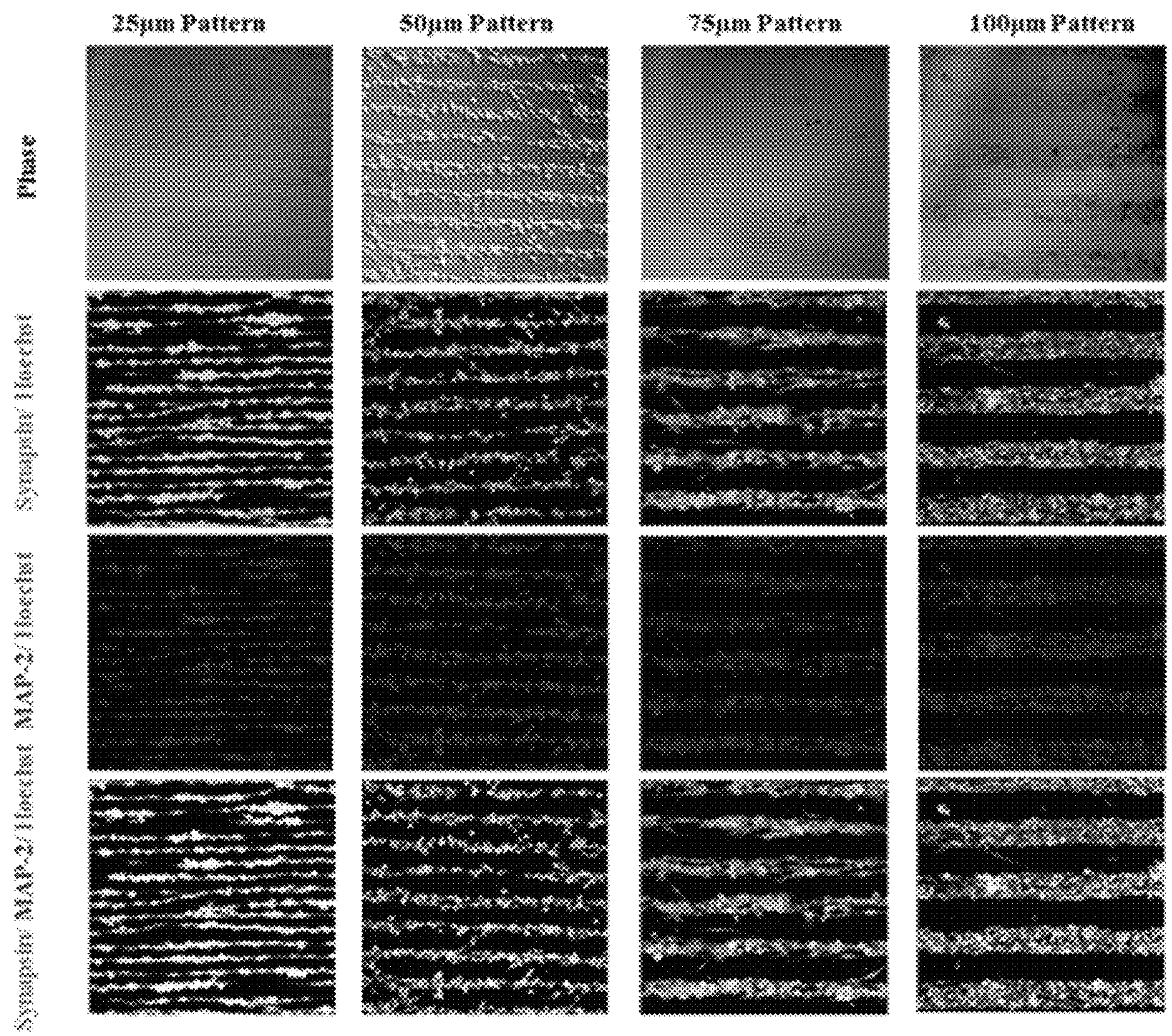

The top panel of FIG. 2D shows a schematic diagram illustrating the manufacturing of magnetic/graphene hybrid nanostructures. The magnetic/graphene hybrid nanostructures were manufactured by treating 10 nm-sized magnetic nanoparticles with 3-aminopropyl triethoxysilane (APTES) to modify a surface of the magnetic nanoparticles to exhibit an amine group and then allowing amine group-introduced magnetic nanoparticles to react with graphene oxide nanoflakes selected through ultrasonication and centrifugation. The bottom panel of FIG. 2*d* shows a schematic diagram illustrating a procedure in which the horizontal growth of neurons was induced by fine-contact printing magnetic/graphene hybrid nanostructures on a substrate, seeding neurons on the nanostructures, and then culturing the neurons under the application of electricity.

Figure 2E:
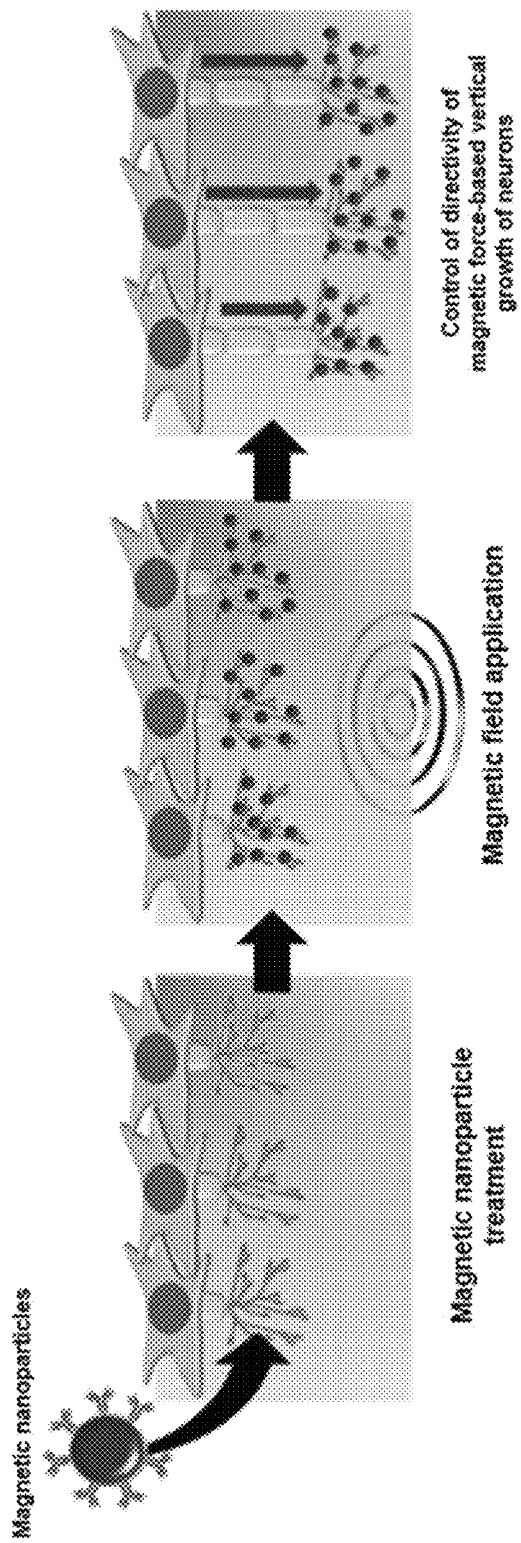

FIG. 2E illustrates an SEM image (scale bar: 20 nm) of the magnetic/graphene hybrid nanostructures and a particle size thereof.

Figure 2F:
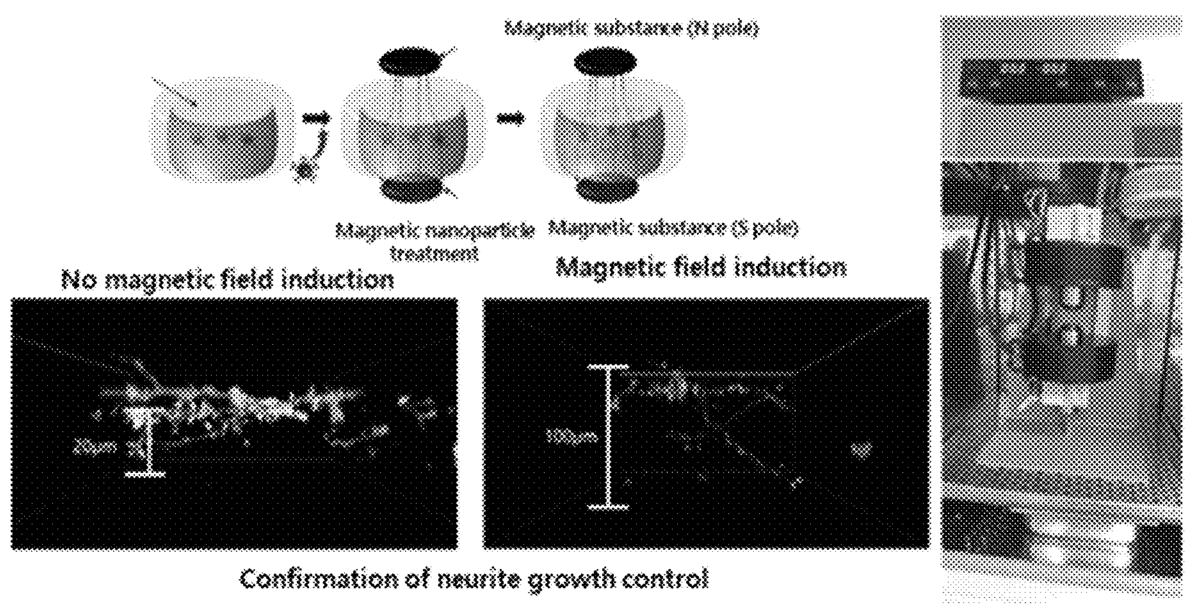

FIG. 2F illustrates a micro-contact printing procedure using magnetic/graphene hybrid nanostructures depending on the presence or absence of magnetic force.

Figure 2G:
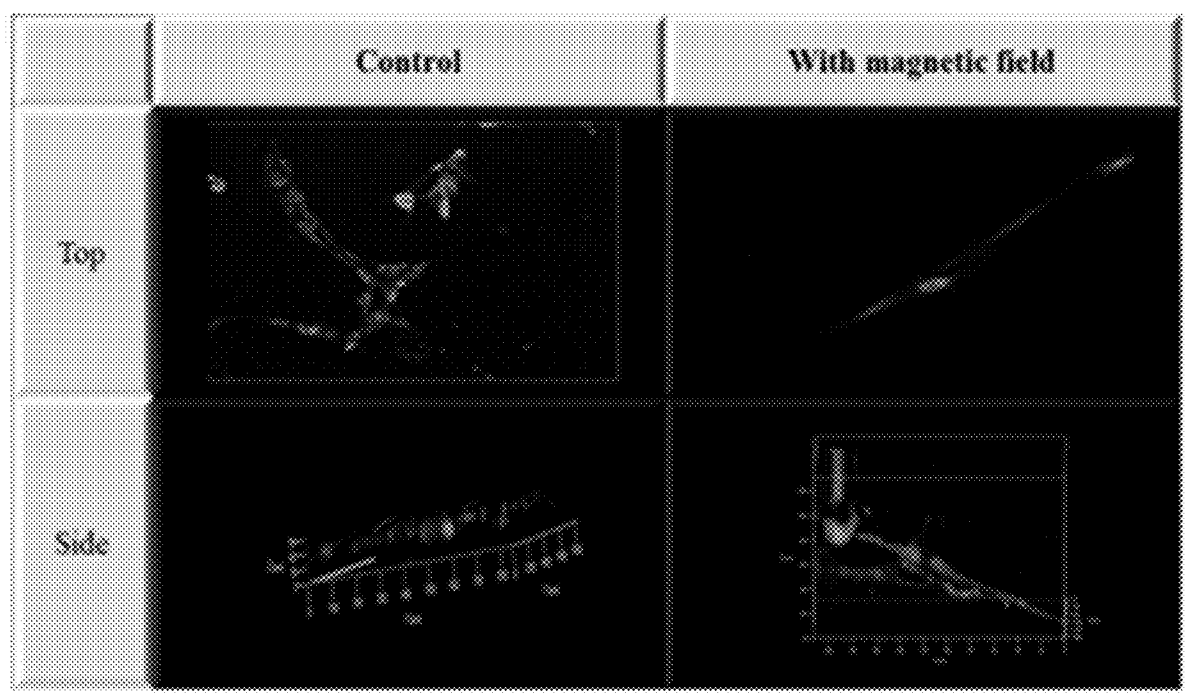

FIG. 2G illustrates the results that the horizontal growth of neurons was induced in regions in which the magnetic/graphene hybrid nanostructures were micro-contact printed.

Figure 3A:
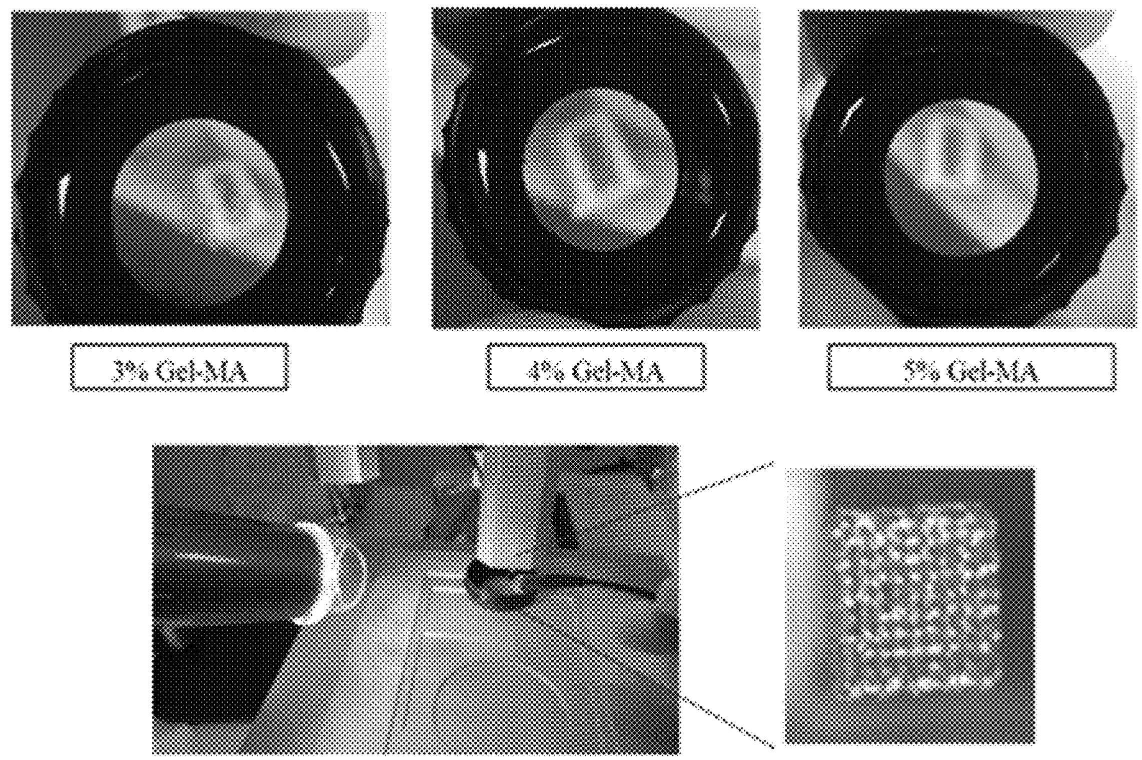

FIG. 3A illustrates the results of confirming structural stability in culture media after neurons were printed on 3%, 4%, and 5% gelatin-methacrylate (Gel-MA).

Figure 3B:
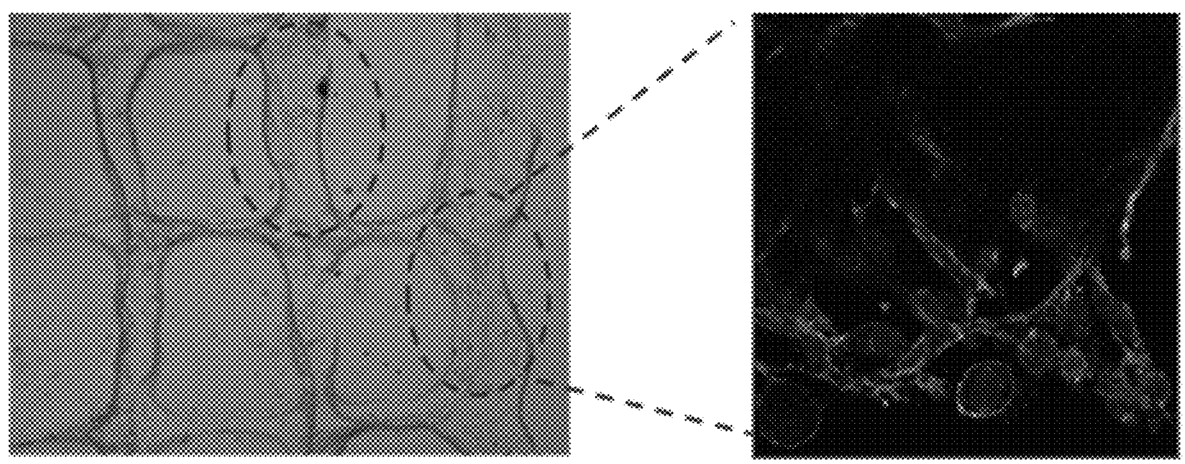

FIG. 3B illustrates the results that neurons printed on 4% Gel-MA formed neural networks.

Figure 3C:
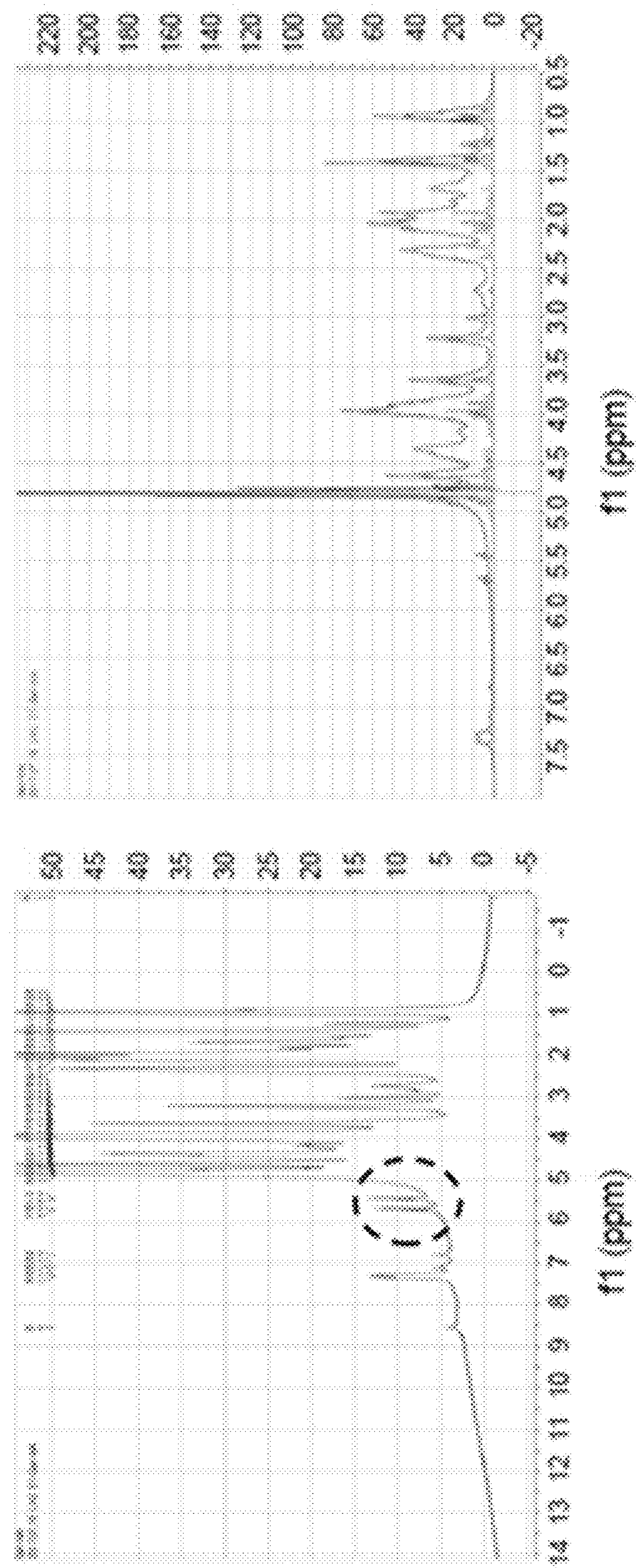
Figure 3C:
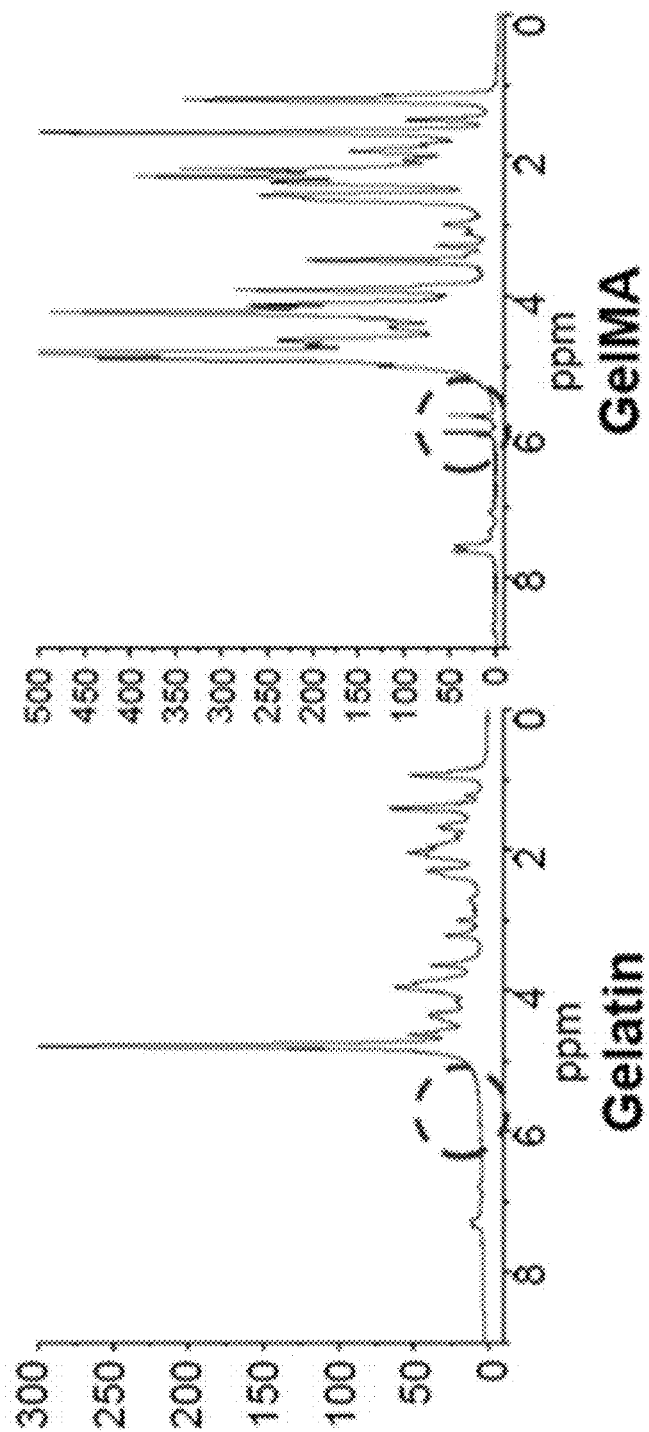

FIG. 3C shows H-NMR results of gelatin and Gel-MA. The red dotted circles represent a peak of methacrylate. The left graph shows an NMR peak of gelatin itself, and the right graph shows that the synthesis of gelatin and methacrylate was well done by confirming peaks of Gel-MA after methacrylate was synthesized in gelatin.

Figure 3D:
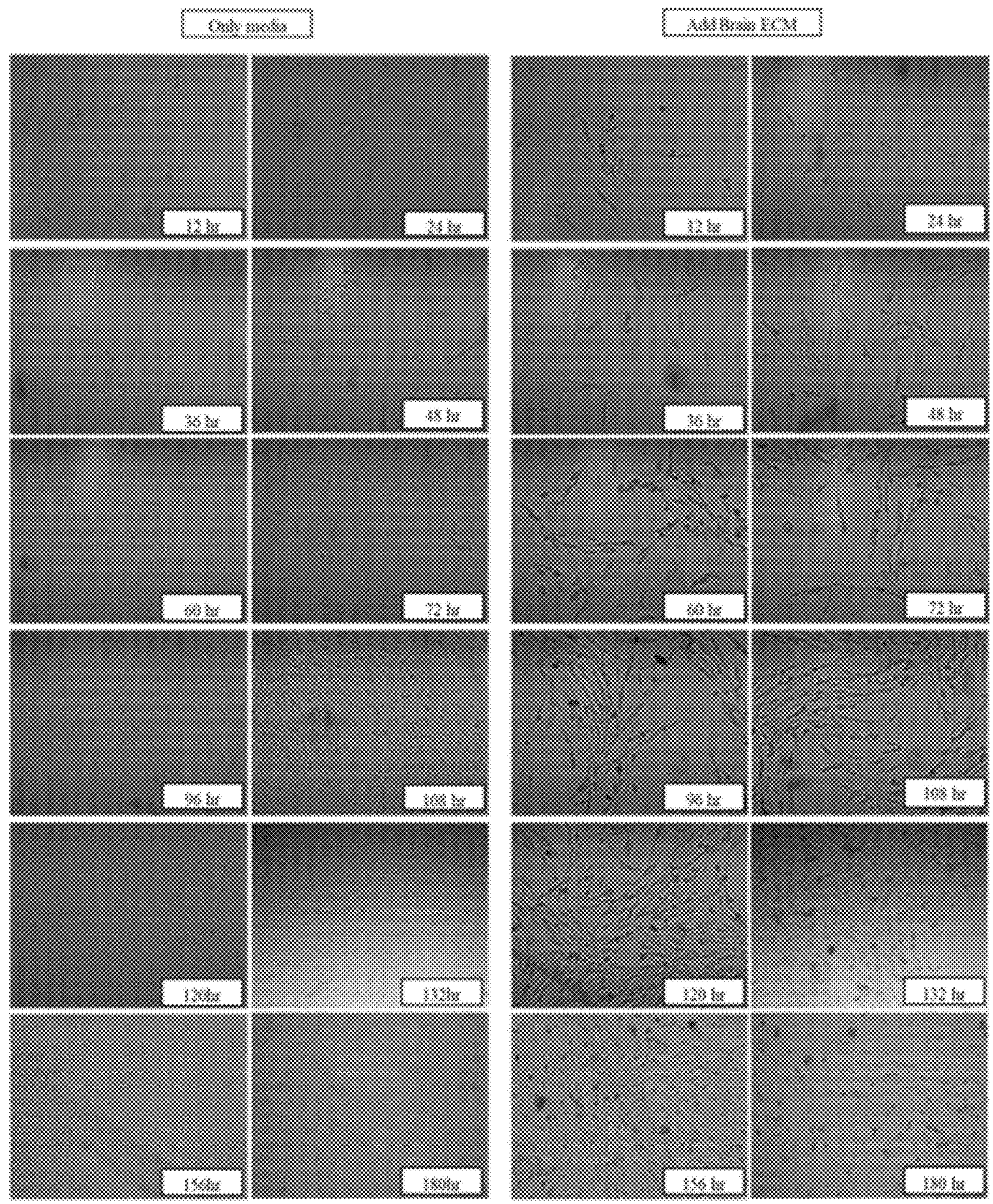

FIG. 3D illustrates the cell morphology of SH-SY5Y according to the culture time in media containing decellularized porcine brain Matrix (DECM).

Figure 4A:
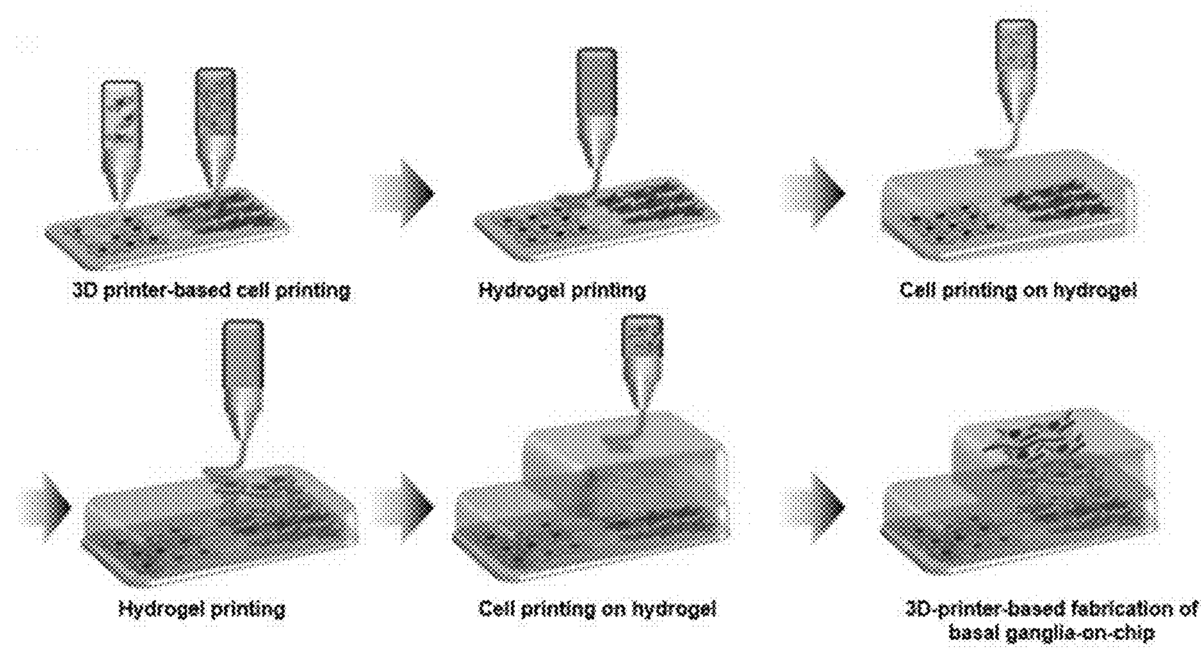

FIG. 4A is a schematic diagram illustrating that a structure of the basal ganglia was mimicked and printed using a 3D cell printer.

Figure 4B:
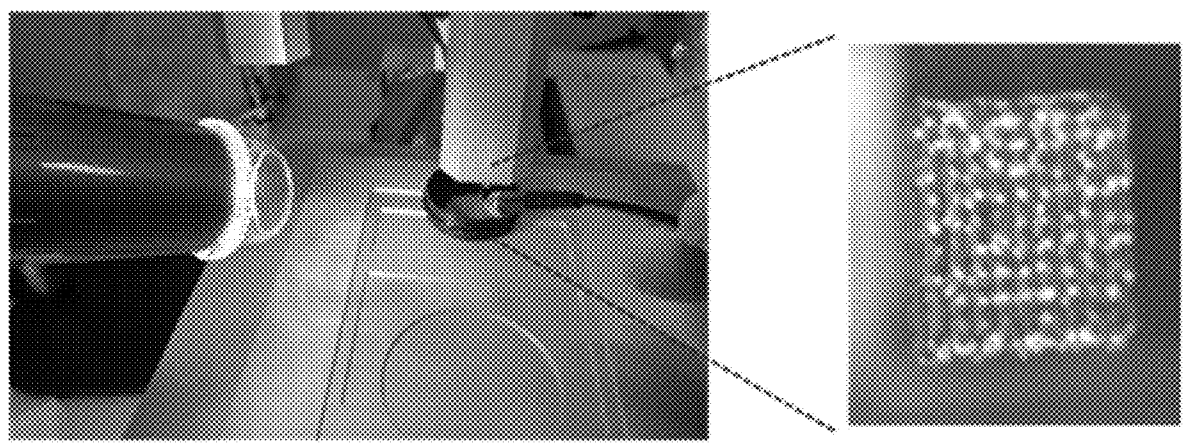

FIG. 4B shows printing images obtained utilizing a 3D printer. The left image illustrates printing using a 3D cell printer, and the right image shows a printed Gel-MA image.

Figure 4C:
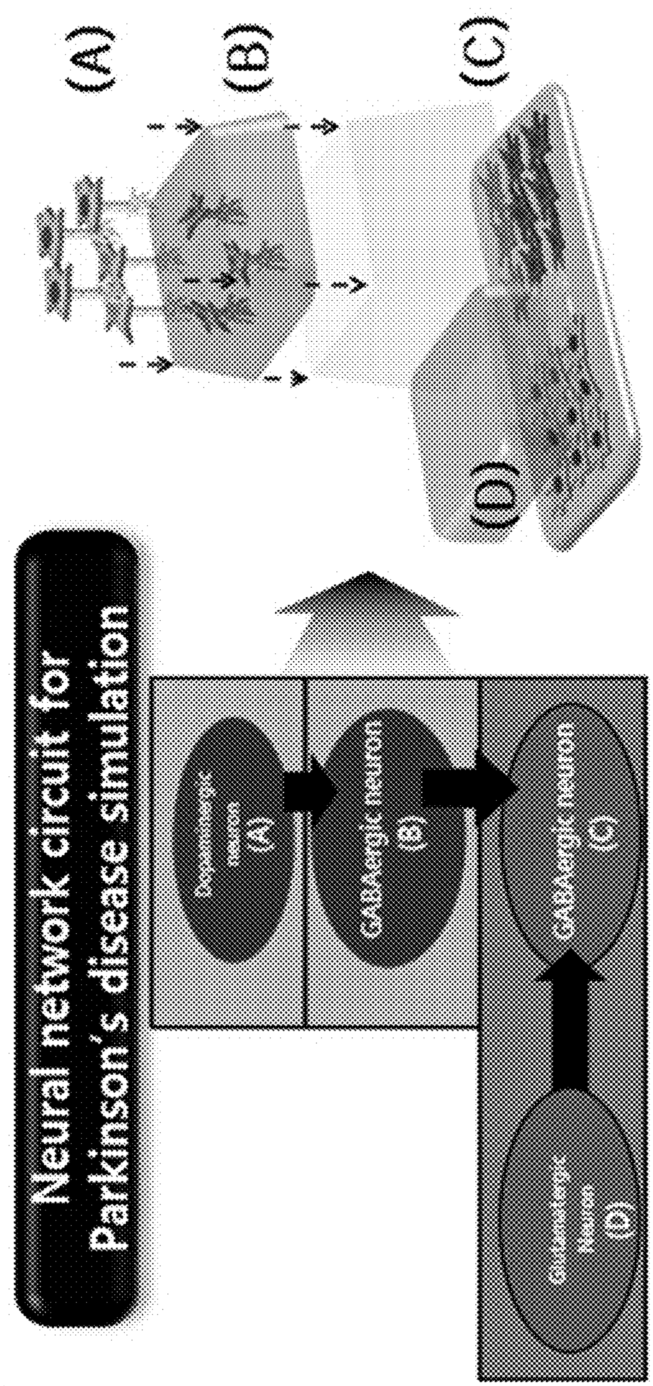

FIG. 4C is a schematic diagram of a Parkinson's disease-like basal ganglia structure.

Figure 4D:
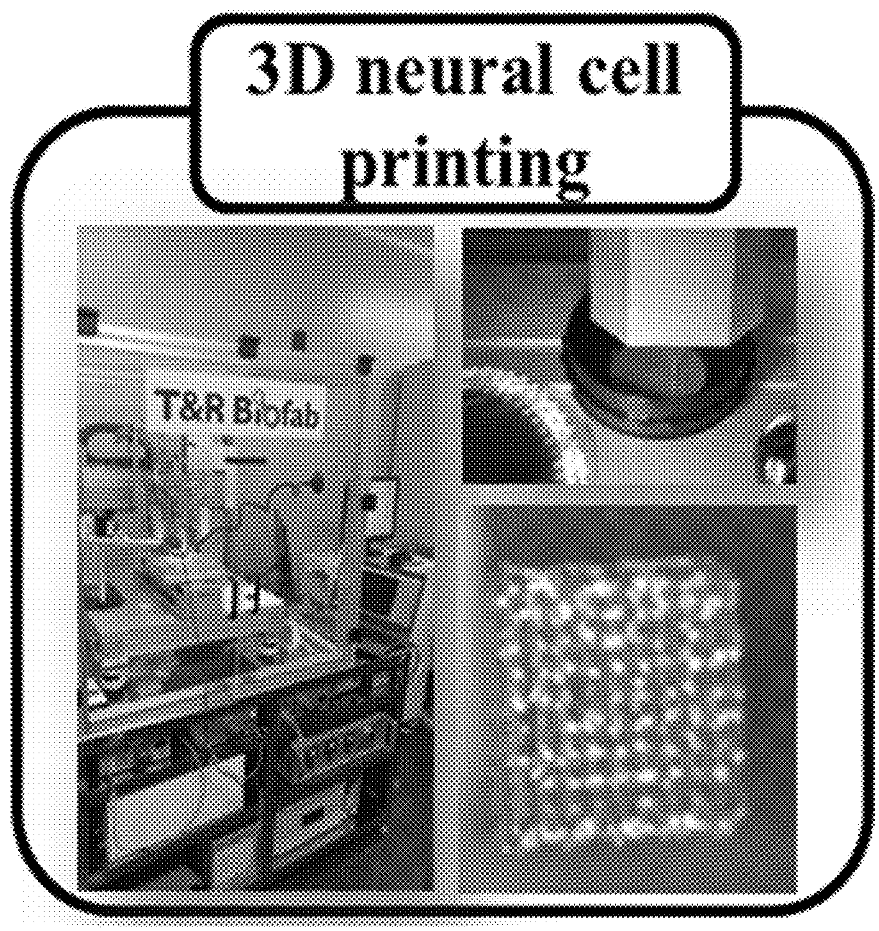

FIG. 4D shows a 3D printer-based basal ganglia-on-a-chip.

Figure 5A:
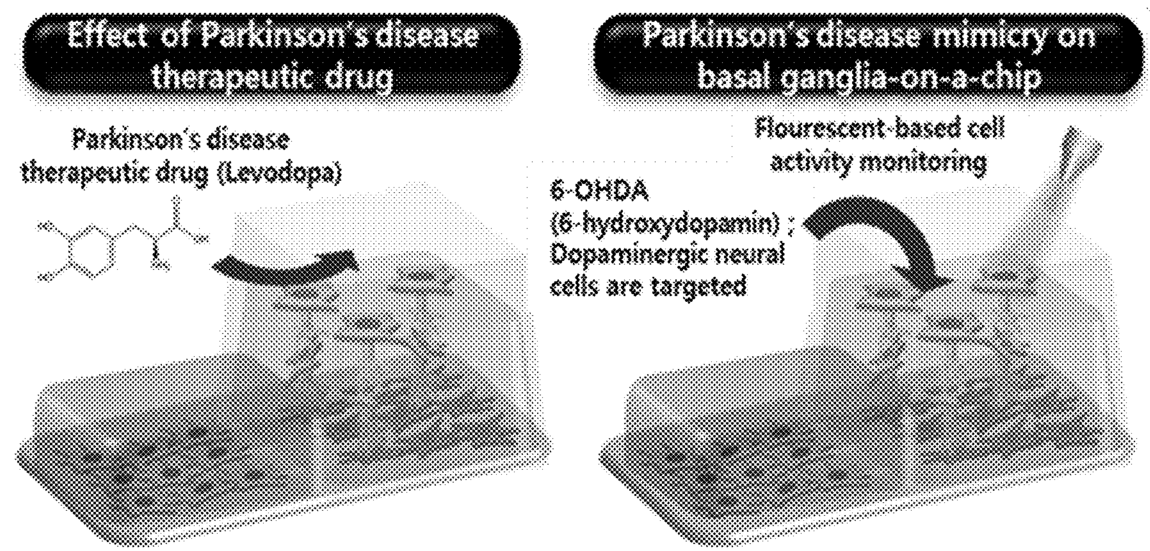

FIG. 5A is a schematic diagram illustrating the treatment of a Parkinson's disease-like basal ganglia structure with L-dopa or 6-OHDA.

Figure 5B:
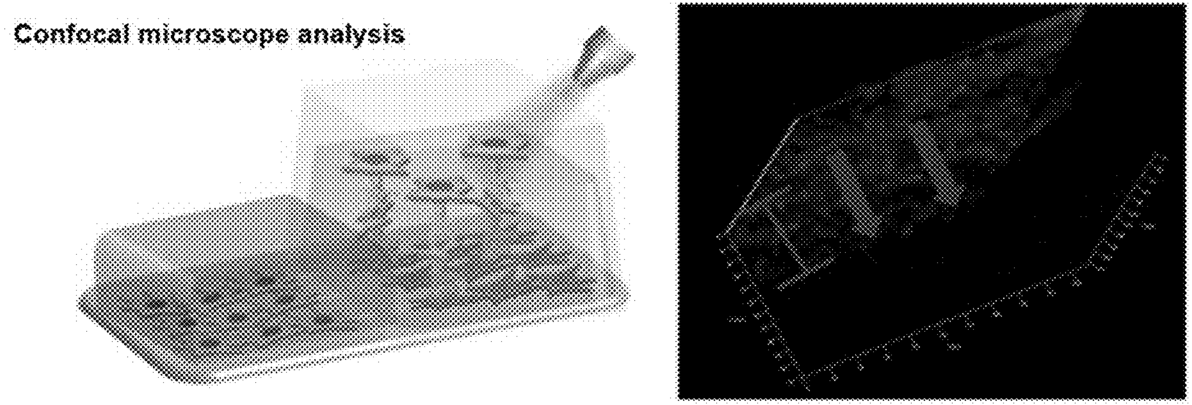

FIG. 5B shows an image of a basal ganglia structure simulating neural structure observed by a confocal microscope. The right image confirms through a confocal microscope that dopaminergic neurons and GABAergic neurons are connected vertically relative to each other.

Figure 5C:
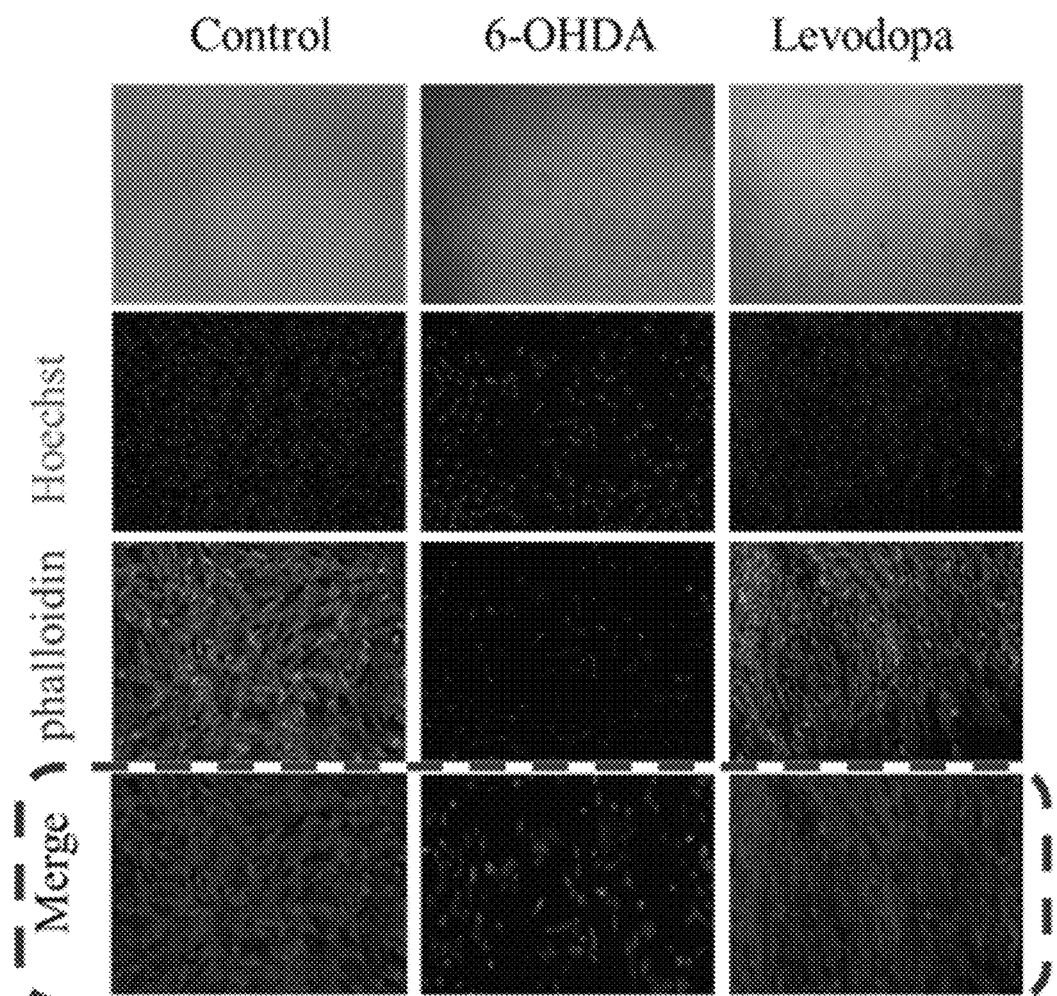

FIG. 5C illustrates an increase in the proliferation of dopaminergic neurons by the treatment of Parkinson's disease-like basal ganglia structure with L-dopa.

DETAILED DESCRIPTION

Hereinafter, the present invention will be described in more detail with reference to examples. These examples are only for illustrating the present invention more specifically, and it will be apparent to those skilled in the art that the scope of the present invention is not limited by these examples.

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

EXAMPLE 1

Design of Simplified Neural Circuit in Basal Ganglia-on-Chip Model

The basal ganglia are composed of various types of neurons, and have various complex neural circuits involved in motor and sensory regulation. The neural circuit has a "direct neural circuit (direct pathway)", in which the behavior evoking neural transmission is made through an excitatory neurotransmission pathway, and an "indirect neural circuit (indirect pathway), in which the behavior evoking neural transmission is made through an inhibitory neurotransmission pathway, and it has been reported that such a neural circuit is involved in neurodegenerative brain diseases, such as Parkinson's disease and Huntington's chorea disease. Especially, Parkinson's disease, which is one of the neurodegenerative brain diseases, is caused by abnormal secretion of gamma-aminobutyric acid (GABA) from the globus pallidus interna (GPi) and substantia nigra reticulate (SNr) due to dysfunction of a direct neural circuit resulting from the apoptosis of dopamine-producing neurons in the substantia nigra pars compacta (SNc) located in the basal ganglia.

Figure 1A:
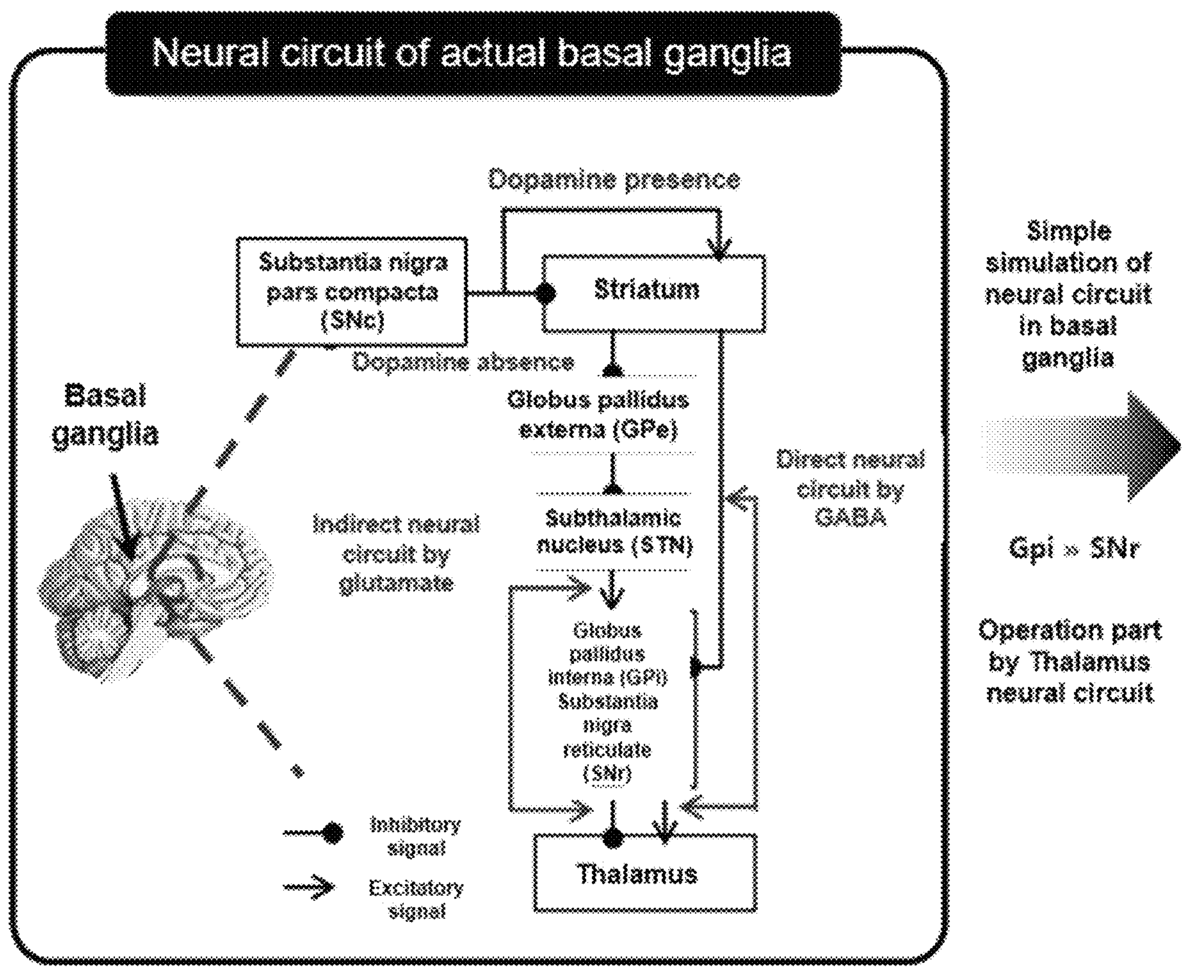
FIG. 1A illustrates a neural circuit of the basal ganglia. The neural circuit is composed of an "indirect neural circuit by glutamate" and a "direct neural circuit by GABA". In Parkinson's disease, the direct neural circuit is inhibited through specific apoptosis of dopamine-producing neurons.
Figure 1B:
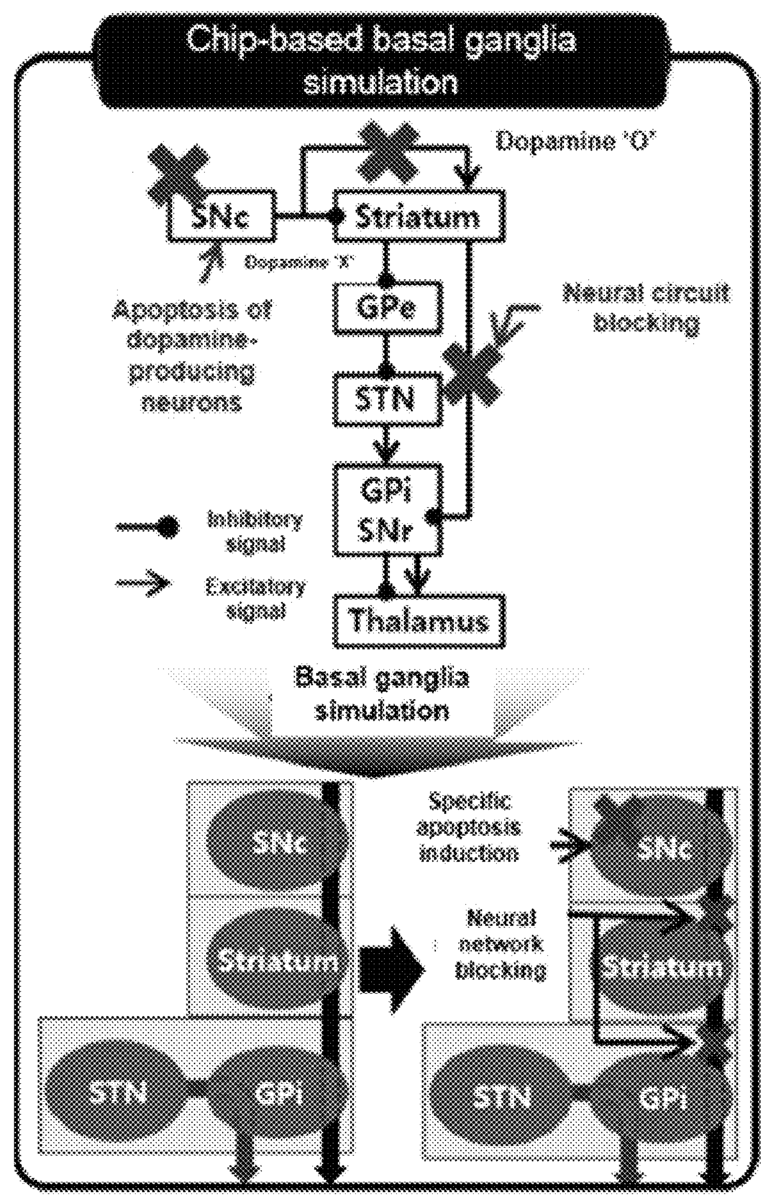
FIG. 1B illustrates a neural circuit simulating a Parkinson's disease-like model inducing specific apoptosis of dopamine-producing neurons.

As for a basal ganglia-on-a-chip model to be developed in the present study, the present inventors designed a neural circuit of a basal ganglia-on-a-chip model as shown in FIG. 1 in order to develop a basal ganglia-on-a-chip model in which a neural circuit associated with Parkinson's disease is simplified and simulated on a chip, and thus a normal neural circuit is simulated thereon, and a Parkinson's disease-like model in which the apoptosis of dopamine-producing neurons is simulated.

EXAMPLE 2

Control of Growth Direction of Magnetic Nanoparticle-Based Neurons

In order to form vertical/horizontal neural networks for the fabrication of a basal ganglia simulating structure, a technique capable of controlling growth directivity of neurons is needed. A method was made that induces the vertical/horizontal growth of neurons by attaching magnetic nanoparticles to neurons, followed by culturing in hydrogel (4% gelatin methacrylate), and then applying a magnetic field in vertical/horizontal directions (FIG. 2).

For the induction of the vertical/horizontal growth of neurons, zinc ferrite nanoparticles, corresponding to a strong magnetic substance having excellent reactivity to a magnetic field, were synthesized. To a 3-neck flask, 2 mmol $Fe(acac)_3$, 1 mmol $ZnCl_2$, 6 mmol oleylamin, 6 mmol oleic acid, and 10 mmol 1,2-hexadecanediol were added, and then 20 ml of trioctylamine as a buffer was added. After being kept at 200° C. for 2 hours, the solution was heated at 300° C. and then kept for 1 hour. Thereafter, 100% ethanol and the synthesized material MNP (zinc ferrite nanoparticles) were mixed at a ratio of 3:1, followed by centrifugation. Then, the supernatant was discarded, and hexane as a buffer was added, and centrifugation was repeatedly performed three times to determine the size of particles. An amine group was formed on a surface of the synthesized zinc ferrite nanoparticles by the treatment with (3-aminopropyl)triethoxysilane (APTES). The amine group on the surface of the zinc ferrite nanoparticles and the N-terminus of the anti-noradrenaline transporter antibody (Sigma-Aldrich) were attached to each other using a 1-ethyl-3-(3-dimethylaminopropyl)-carbodiimide/N-Hydroxysuccinimide (EDC/NHS) coupling method, thereby synthesizing magnetic nanoparticles capable of attaching to neurons.

The magnetic nanoparticles-attached neurons were cultured on a hydrogel (4% gelatin methacrylate), and after 24 hours, a magnetic field was applied for 7 days to induce the vertical growth of neurons. According to an existing method, a magnetic field was formed using a neodymium magnet, but for the accuracy of an experiment, a magnetic field forming device was provided to apply a constant magnetic field at the level (400-450 mT) similar to that of a neodymium magnet, thereby inducing the vertical growth of neurons, and thus the accuracy of the experiment was improved. A magnetic field was applied using the magnetic field forming device for about 5-7 days to induce directivity, thereby forming neural networks between dopaminergic neurons and GABAergic neurons (FIG. 2*b*).

After the vertical growth was induced, fluorescein isothiocyanate (FITC) attached to the anti-noradrenaline transporter antibody was imaged using a confocal microscope to conform that the neurons were induced to grow in a direction in which the magnetic field was applied, and it was confirmed that neurons continued without breakage upon the induction of vertical growth of neurons (FIG. 2).

Also, for the induction of horizontal growth, 10 nm-sized magnetic nanoparticles were treated with APTES such that a surface of the magnetic nanoparticles was modified to exhibit an amine group (FIG. 2*d*). The amine group-introduced magnetic nanoparticles were subjected to ultrasonication and centrifugation, so that the magnetic nanoparticles bunched together were separated from each other to utilize magnetic nanoparticles as small as possible (FIG. 2*e*). The selected magnetic nanoparticles were allowed to react with graphene oxide (combination of the amine group of APTES attached to the magnetic nanoparticles and the carboxyl group of GO) to manufacture magnetic/graphene hybrid nanostructures. Specifically, a 5% APTES solution was mixed at a ratio of 1:1 with a solution obtained by diluting 5 mg/ml magnetic nanoparticles to 1/10. The mixture was maintained at 25° C. for 30 min in a stirrer. In addition, a solution obtained by diluting a 1 g/L graphene oxide solution to 1/2 was allowed to react with a magnetic nanoparticle solution reacted with APTES at 25° C. for 30 min in a stirrer.

Linear magnetic/graphene patterns were manufactured on a polydimethylsiloxane (PDMS) substrate using the magnetic/graphene hybrid nanostructures by micro-contact printing method using PDMS stamp. As a result of micro-contact printing, it was confirmed through the SEM images that the magnetic/graphene hybrid nanostructure linear patterns were more clearly formed in the presence of magnetic force, and thus the micro-contact printing method with the application of magnetic force is a more suitable method for inducing the horizontal growth of cells (FIG. 2*f*). It was confirmed through an optical microscope that neurons were well immobilized in regions in which the magnetic/graphene hybrid nanostructures were micro-contact printed, but the cells hardly grew in regions in which the magnetic/graphene hybrid nanostructures were not micro-contact printed.

Linear magnetic/graphene patterns with different intervals and thicknesses were formed on the PDMS through a micro-contact printing technique utilizing PDMS stamps with different intervals and thicknesses. Thereafter, as a result of culturing neurons, it was confirmed that the neurons were cultured along the magnetic/graphene patterns (FIG. 2*g*).

EXAMPLE 3

Manufacturing of Bio-Ink to be Used in 3D Cell Printing and Fabrication of Basal Ganglia-on-a-Chip Model A hydrogel is needed to mimic the basal ganglia using a 3D cell printer on the basis of a vertical/horizontal network forming technique. The gelatin-methacrylate harmless to cells was synthesized. After 10% gelatin (Sigma-Aldrich) was completely dissolved in Dulbecco's phosphate-buffered saline (DPBS), 0.4 ml/g methacrylate (Sigma-Aldrich) was slowly added (0.1 mL/g), followed by reaction at 50° C. for about 4 hours. Thereafter, the total concentration was adjusted to 4.5% with DPBS, followed by dialysis. After the dialysis was completed, the resultant material was frozen at −80° C. for about one day and then freeze-dried for 7 days. The synthesis was investigated through H-NMR (FIG. 3*c*). It is very important that the printed structure of the synthesized gelatin methacrylate is held without collapse until neurons can grow to form networks. Accordingly, it was investigated how long the structure was held after the structure was manufactured by preparing 3%, 4%, and 5% gelatin methacrylate and cell-printing the gelatin methacrylate using a 3D cell printer. It was confirmed that a structure of 4% gelatin methacrylate was held without collapse for 72 hours or longer (FIG. 3*a*). A factor that is as important as the structure being held is that neurons in the hydrogel well stretch and grow to form neural networks. Thus, the cell growth was observed by printing gelatin methacrylate in a grid pattern using a 3D cell printer. The cell printing was performed using 4% gelatin methacrylate, and then the neurons were grown for 4 days, stained, and observed through a confocal microscope. As a result, it was confirmed that the neurons well grew and stretch in the gelatin methacrylate (FIG. 3*b*). The 3% gelatin methacrylate was structurally unstable in culturing neurons due to a disadvantage that the structure collapses after about 2 days. The 5% gelatin methacrylate is unsuitable for the growth of neurons due to a disadvantage that the gelatin methacrylate floats in media. Therefore, a basal ganglia-on-a-chip was fabricated by using the 4% gelatin methacrylate having structural stability suitable to culture neurons and containing a hydrogel well attached to the bottom of a culture dish. The decellularized porcine brain matrix (DECM) extracted from the porcine brain was dissolved at a concentration of 0.1 mg/mL in a culture medium, and then the resultant medium, instead of an existing culture medium, was added to gelatin methacrylate every 12 hours to grow neurons.

As for the DECM, the fresh porcine brain was directly purchased, and added to penicillin-containing PBS and sodium dodecyl sulfate (SDS, 0.1 wt/vol), and decellularized for 3-5 days while the supernatant was exchanged. After centrifugation using a centrifuge at 10,000 rpm/5 min, the supernatant was removed, followed by filling with tertiary distilled water. After this procedure was repeated about 12 times, the DECM was freeze-dried, and used if needed while stored at −80° C. The prepared DECM at 0.1 mg/ml was added to DMEM containing 10% FBS and 1% penicillin, which was replaced for an existing culture medium every 24 hours while neurons were cultured. Compared with the neurons grown in an existing culture medium without the supplementation of DECM, the neurons (SH-S5SY) cultured in the DECM-supplemented culture medium showed a different growing form, a drop in the neuron proliferation rate as if the neurons differentiated, and long stretched axons (FIG. 3*d*).

In order to fabricate a basal ganglia-on-a-chip, SH-SY5Y (ATCC CRL-2266) was used as dopaminergic neurons, and F3-NG1 (provided from professor Hong-Joon Lee at Chung-Ang University) were allowed to differentiate and then used as GABAergic neurons and glutamatergic neurons.

The SH-SY5Y was cultured using DMEM/F12 containing 3% FBS, 1% penicillin/streptomycin, and 1 μM retinoic acid (RA) while the medium was exchanged at intervals of 2 days.

For the differentiation of F3-NG1 into GABAergic neurons, the cells were cultured in a medium for differentiation (DMEM/F12 supplemented with 10% FBS and 1 penicillin) for 1 day, a medium for differentiation containing B27 (1×), N2 (1×), 20 ng/ml basic fibroblast growth factor (bFGF), and 5 μM valproic acid (VPA) for 2 days, and a medium for differentiation containing B27 (1×), 20 ng/ml brain-derived neurotrophic factor (BDNF), 20 ng/ml glial cell line-derived neurotrophic factor (GDNF), 20 ng/ml IGF, and 1 mM AA for 4-10 days.

For the differentiation of F3-NG1 into glutamatergic neurons, the cells were cultured in a medium for differentiation containing B27 (1×), N2 (1×), and 20 ng/ml basic fibroblast growth factor (bFGF) for 1 day, and a medium for differentiation containing B27 (1×), N2 (1×), 20 ng/ml BDNF, and 100 ng/ml GDNF for 4-10 days.

As for the bio-ink used in the experiments in the present invention, the synthesized Gel-MA was made to 4% by addition of DPBS, and the 4% Gel-MA was used by mixing with cells (0.033 mg/mL). The use of the bio-ink containing DECM was expected to significantly accelerate the stretching of cells or the growth rate thereof.

Based on such a technique, a basal ganglia-on-a-chip can be fabricated by using neurons and gelatin methacrylate through a 3D cell printer.

EXAMPLE 4

Fabrication of Basal Ganglia-on-a-Chip-Based Parkinson's Disease-Like Model and Drug Screening Parkinson's disease is caused by the gradual loss of dopaminergic neurons distributed in the substantia nigra. 6-Hydroxydopamine (6-OHDA) causes oxidative stress to induce mitochondrial migration of c-Jun N-terminal kinase (JNK), and the activated JNK after mitochondrial migration causes mitochondrial dysfunction, contributing to apoptosis of dopaminergic neurons, occurring in Parkinson's disease.

Based on this, a Parkinson's disease model was developed using 100 μM 6-OHDA. After the Parkinson's disease-like model was established, 50 μM Levodopa (L-dopa), and the proliferation of dopaminergic neurons was confirmed by artificially increasing the amount of L-dopa. These results indicate that the efficacy of therapeutic agents for treating dopamine-related diseases could be evaluated by using the Parkinson's disease-like model-based basal ganglia-on-a-chip of the present invention.

Considering the above results, the basal ganglia are well simulated, and drug screening for a short time can be attained using a basal ganglia-on-a-chip model without animal experiments or clinical tests. Furthermore, on the basis of this technique, organs-on-chips could be fabricated, and several disease models can be implemented, such as a cerebral cortex-on-a-chip.

What is claimed is:

1. A basal ganglia-on-a-chip for screening therapeutic agents for dopamine-dependent brain and nervous system diseases, the basal ganglia-on-a-chip comprising:

graphene-conjugated magnetic nanoparticles patterned on a substrate;

a first layer comprising (i) a first hydrogel containing glutamatergic neurons and (ii) a second hydrogel containing GABAergic neurons, the first and second hydrogels being disposed in parallel on a pattern of the graphene-conjugated magnetic nanoparticles;

a second layer comprising a third hydrogel in contact with the second hydrogel, the third hydrogel containing GABAergic neurons and neuronal membrane protein-specific antibody-conjugated magnetic nanoparticles; and a third layer comprising a fourth hydrogel in contact with the third hydrogel, the fourth hydrogel containing dopaminergic neurons and neuronal membrane protein-specific antibody-conjugated magnetic nanoparticles, wherein the third hydrogel is on the second hydrogel and the fourth hydrogel is on the third hydrogel, and wherein the GABAergic neuron of the third hydrogel and the dopaminergic neurons of the fourth hydrogel induced vertical growth towards the substrate, wherein the first hydrogel and the second hydrogel have a concentration of gelatin methacrylate (GelMA) of more than 3.0 w/w % and less than 5.0 w/w %, and wherein the GelMA is synthesized by adding 0.4 mL/g methacrylate to Dulbecco's phosphate-buffered saline (DPBS) in which 10 w/v % gelatin is dissolved.

2. The basal ganglia-on-a-chip of claim 1, wherein the third hydrogel to the fourth hydrogel contain at least one hydrogel monomer selected from the group consisting of gelatin methacrylate (GelMA), acrylic acid, acrylamide, N-isopropylacrylamide (NIPAAM), and polyethylene glycol diacrylate (PEGDA).

3. The basal ganglia-on-a-chip of claim 1, wherein the first hydrogel to the fourth hydrogel further contain decellularized brain matrix (DECM).

4. The basal ganglia-on-a-chip of claim 1, wherein the graphene-conjugated magnetic nanoparticles are manufactured by combining a modified amine group on a surface of the magnetic nanoparticle and a carboxyl group of a graphene oxide.

5. The basal ganglia-on-a-chip of claim 1, wherein the antibody specific to cell membrane proteins which is bound to the antibody-conjugated magnetic nanoparticles specific to the neuronal membrane protein is an antibody specific to membrane receptors, transport proteins, membrane enzymes, or cell adhesion molecules in neurons.

6. A method for screening therapeutic agents for brain and nervous system diseases by using the basal ganglia-on-a-chip of claim 1, the method comprising: (a) treating dopaminergic neurons with a candidate of therapeutic agents for brain and nervous system diseases; and (b) investigating whether the dopaminergic neurons proliferate or are reduced.

7. The method of claim 6, wherein the dopaminergic neurons are induced to have damages.

8. The method of claim 7, wherein the damages are caused by oxidative stress.

9. The method of claim 6, wherein the dopaminergic neurons are induced to differentiate.

* * * * *